United States Patent [19]
Field et al.

[11] 4,194,049
[45] Mar. 18, 1980

[54] 2-[[2-METHYL-1-[2-BENZOYL(OR BENZYL)PHENYL]-1H-IMIDAZOL-5-YL]METHYL]-1H-ISOINDOLE-1,3(2H)-DIONES

[75] Inventors: George F. Field, West Caldwell; William J. Zally, Cresskill, both of N.J.

[73] Assignee: Hoffmann-La Roche Inc., Nutley, N.J.

[21] Appl. No.: 25,219

[22] Filed: Mar. 29, 1979

[51] Int. Cl.² ............................................ C07D 403/06
[52] U.S. Cl. .................................. 548/336; 548/324; 548/342; 548/343
[58] Field of Search .......................................... 548/336

[56] References Cited
U.S. PATENT DOCUMENTS 3,941,803 3/1976 Gall ...................................... 548/336

*Primary Examiner*—Natalie Trousof
*Attorney, Agent, or Firm*—Jon S. Saxe; Bernard S. Leon; Frank P. Hoffman

[57] ABSTRACT

A multistep process is presented for the preparation of imidazobenzodiazepines of the formula

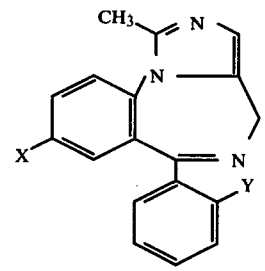

wherein X and Y are selected from the group consisting of hydrogen, halogen and trifluoromethyl.

Also presented are novel intermediates utilized in the process.

The end products are useful as sedatives, anxiolytics, muscle relaxants and anticonvulsants.

The end products are especially useful in intravenous compositions for use in preoperative anesthesia.

2 Claims, No Drawings

2-[[2-METHYL-1-[2-BENZOYL(OR BENZYL)PHENYL]-1H-IMIDAZOL-5-YL]METHYL]-1H-ISOINDOLE-1,3(2H)-DIONES

DESCRIPTION OF THE INVENTION

The present invention relates to a process to produce imidazobenzodiazepines of the formula

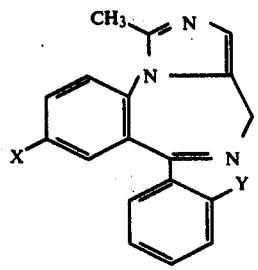

wherein X and Y are selected from the group consisting of hydrogen, halogen and trifluoromethyl.

The imidazobenzodiazepines are useful as sedatives, anxiolytics, muscle relaxants and anticonvulsants, a description of these compounds can be found in Belgian Pat. No. 839,364 which is incorporated herein by reference.

As utilized in the present specification, the terms "halo" or "halogen" mean all four forms thereof, i.e., chlorine, bromine, iodine and fluorine, except where otherwise indicated.

As utilized herein the term "lower alkyl" means a $C_1$ to $C_7$ straight or branched chain, preferably $C_1$ to $C_4$, carbon-hydrogen radical.

The following reaction scheme sets forth the novel process which is less expensive and less hazardous than previous prior art processes.

Reaction Scheme

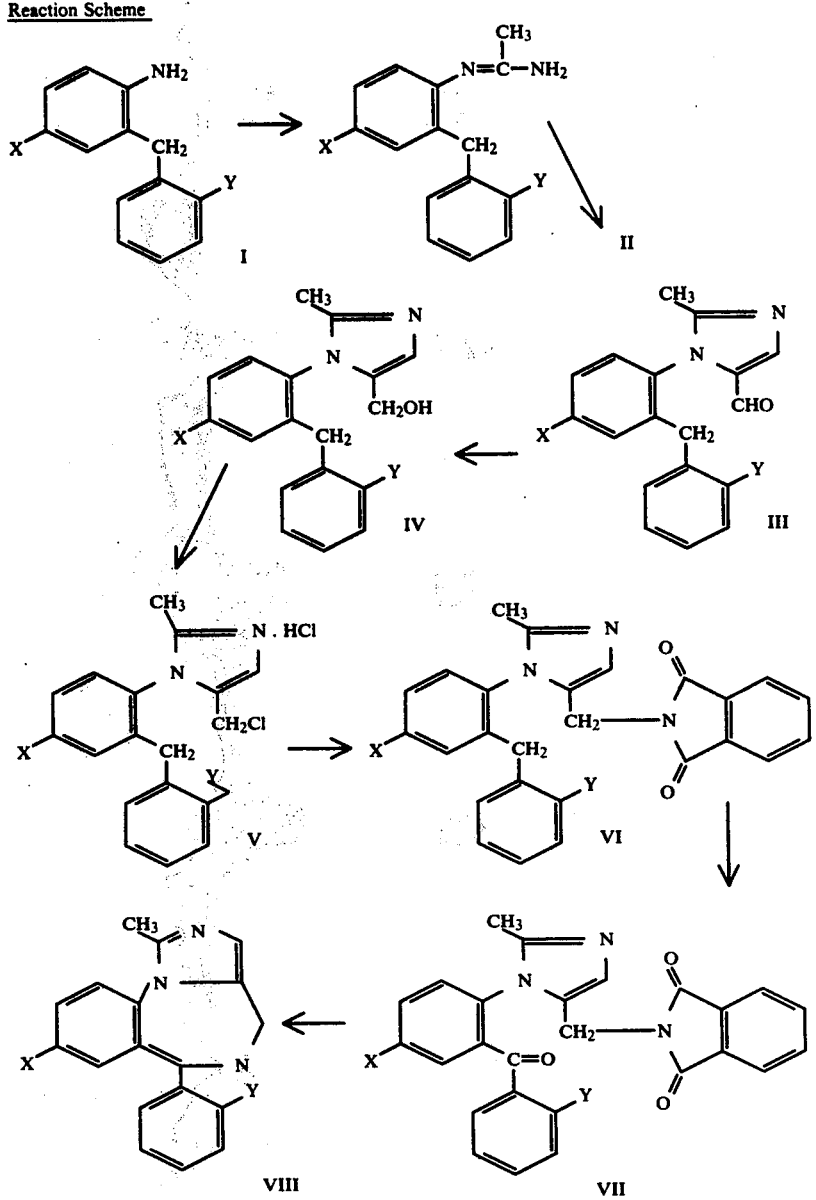

wherein X and Y are selected from the group consisting of hydrogen, halogen and trifluoromethyl.

I→II

The compound of formula I may be produced following an analogous method to that described by Gassman et al. in Chemical Communications, 1973, p. 488. A further reference which describes the desfluoro analog of the compound of formula I may be found in Gall et al., J. Med. Chem., 19, 1057, 1976.

The compound of formula I is thereafter reacted with a Lewis Acid such as hydrochloric acid, zinc chloride or aluminum chloride and acetonitrile. Suitable solvents for such a reaction would be inert organic solvents such as tetrahydrofuran, methylene chloride, benzene, toluene or excess acetonitrile. The reaction temperature may vary from about room temperature to 150° C. with about the reflux temperature of the solvent as preferred.

II→III

The compound of formula II is thereafter reacted with a halomalonaldehyde such as bromomalonaldehyde in an inert organic solvent such as a $C_1$ to $C_4$ alcohol e.g., ethanol, tetrahydrofuran or dimethylformamide. The reaction temperature can range from about room temperature to reflux with about reflux temperature of the selected solvent as preferred. A buffer such as triethyl ammonium acetate may be added.

III→IV

The compound of formula III is reacted with a metal hydride reducing agent such as lithium aluminum hydride or sodium borohydride in the presence of a solvent such as a $C_1$ to $C_4$ alcohol, e.g., ethanol or a low boiling ether such as dioxane. The reaction temperature may be varied from about 0° C. to 80° C. with room temperature as preferred.

IV→V

The compound of formula IV is reacted with a halogenating agent, such as, thionyl chloride, phosphorus oxychloride or phosphorus trichloride in a chlorinated hydrocarbon solvent, such as, chloroform or methylene chloride or other inert organic solvents, such as, benzene or toluene. The reaction temperature may range from about 0° C. to 100° C. with about 50° C. to 60° C. as a preferred range.

V→VI

The compound of formula V is thereafter neutralized with a base, such as, an alkoxide, e.g., sodium or potassium, methoxide, potassium t-butoxide, an alkali metal carbonate, e.g., sodium or potassium carbonate. Thereafter there is added an alkali metal phthalimide, such as, potassium phthalimide. The reaction temperature may be varied between about 0° C. to 100° C. with about room temperature as preferred.

VI→VII

The compound of formula VI is reacted with chromium trioxide or chromic acid in an acetic acid/water mixture at a reaction temperature of from about 0° C. to 120° C. with reflux temperature, e.g. about 80°-90° C. as preferred.

VII→VIII

The compound of formula VII is thereafter reacted with an aqueous solution of a lower alkyl amine, e.g., methyl amine. A $C_1$ to $C_4$ alcohol is utilized as the solvent with ethanol as preferred. The reaction is most preferably carried out at about room temperature. The final product is isolated thereafter by utilizing well-known filtration techniques.

The following examples are illustrative of the present invention and are not intended to limit the scope thereof.

EXAMPLE 1

2-Amino-5-chloro-α-(2-fluorophenyl)benzenemethanol

To 2.5 l. of 2-propanol in a 5 l. three-necked flask fitted with a stirrer and a reflux condenser is added 500 g (2 moles) of 2-amino-5-chloro-2'-fluorobenzophenone. This mixture is stirred and heated to ca 60° C. when of the starting material should be in solution. The 25 g (0.66 mole, 2.64 eq) of sodium borohydride is added. The reaction mixture is stirred and heated under reflux for 1 hr. TLC($CH_2Cl_2$) should show little or no starting ketone. The reaction is allowed to cool slightly and transferred to a 12 l. enamel pot containing a mechanical stirrer. 50 ml of glacial acetic acid is then added. A gelatinous precipitate forms. This mixture is diluted with 6 l. of water in portions. With the first addition the gelatinous precipitate dissolves. Addition is continued until the solution becomes cloudy. It is then scratched, seeded, and allowed to stir until a granular precipitate forms. The rest of the water is then added in portions allowing time for coagulation of the precipitate between additions. The mixture is stirred 1.5 hr after the last addition of water. The product is then collected, washed with water and then with 500 ml of hexane. It is sucked thoroughly dry on the funnel and spread in trays to air dry overnight to give 600–750 g of crude product which is used as is in the next step. An analytical sample prepared by recrystallization from aqueous methanol had m.p. 94°–98° C.

EXAMPLE 2

4-Chloro-2-[(2-fluorophenyl)methyl]benzenamine

In a 5 l. three-necked flask fitted with stirrer, reflux condenser and thermometer is placed 2.5 l. of 6 N hydrochloric acid. It is heated to 50°–75° C. and 300–340 g of crude 2-amino-5-chloro- α-(2-fluorophenyl)benzenemethanol from the first example is added to the stirred acid. A dark oil may form. 400–425 g of zinc dust is added in portions with continued heating during 15–20 min. The temperature should be 90°–100° C. The addition of the zinc dust is mildly exothermic. The reaction mixture is then stirred and heated under reflux for 1 hr. TLC(10% MeOH/$CHCl_3$) of an aliquot basified with ammonia and extracted with ether should show little or no starting material and a faster spot due to product. Only traces of zinc should remain. The reaction is cooled in an ice bath with stirring to 5°–10° C. A granular yellowish precipitate forms. This precipitate is collected in a sintered glass funnel and transferred to a 4 l separatory funnel. It is dissolved in 1.5 l. of ether and 500 ml of water. Traces of zinc are ignored. If there is enough to clog the stop cock it may be necessary to filter if off. The mixture is made basic by addition of 300 ml of concentrated ammonium hydroxide. A white precipitate is formed in the aqueous layer and then redissolves. The aqueous layer is separated; the ether layer is washed with 500 ml of water, dried over potassium carbonate, and concentrated in vacuo to leave an orange oil. 250 ml of toluene is added and the solution reconcentrated in vacuo. It is dissolved in 400–500 ml of ether. Gaseous hydrogen chloride is bubbled into this solution, first at room temperature and then with cooling in an ice bath. The mixture becomes cloudy and then with swirling crystals form. When it appears to be saturated with HCl, the mixture is allowed to stand in an ice bath for 1 hr. The solid is collected to give crude product. TLC(10% MeOH/CHCl$_3$, and 25% EtOAc/hexane) should indicate reasonable purity. An analytical sample, m.p. 175°–181° C., was prepared by recrystallization from acetonitrile.

EXAMPLE 3

Bromomalonaldehyde

To a 2 l. three-necked round bottom flask filled with stirrer, thermometer and a 250 ml addition funnel is added 500 g (3.045 mole) of malonaldehyde bis-(dimethyl acetal), 550 ml of water and 22 ml of concentrated hydrochloric acid. The mixture is stirred for 15 min. at r.t. until a clear solution is formed. Then 160 ml (3.11 mole) of bromine is added during 20 min. while cooling the mixture in an ice bath to maintain the temperature at 20°–30° C. The reaction is exothermic, and the bromine color is discharged immediately. It is then stirred for 1 hr at room temperature, and then concentrated in vacuo on the rotary evaporator with the heating bath at 50°–60° C. to ca. 700 ml. The slurry resulting is stored in the refrigerator overnight. The product is collected and washed with 250 ml of cold 50% aqueous methanol in portions. Contact with metal is to be avoided since it discolors. The product is dried in a vacuum oven below 60° C.

EXAMPLE 4

4-Chloro-2[(2-fluorophenyl)methyl]-N-(1-aminoethylidene)benzenamine

In 500 ml three-necked flask fitted with a stirrer, gas inlet tube, and a double condenser is placed 13.65 g (50 mmoles) of 4-chloro-2[(2-fluorophenyl)methyl]benzenamine and 200 ml of acetonitrile. Hydrogen chloride gas is bubbled into this stirred suspension. The temperature rises to ca. 38° C. and a solution is formed in about 10 min. The reaction mixture is then heated to gentle reflux while maintaining a stream of hydrogen chloride throught the reaction mixture. After 1 hr TLC of an aliquent using 2% acetic acid, 10% MeOH in CHCl$_3$ or 1% NH$_4$OH/20% MeOH in CHCl$_3$ on fluorescent silica plates shows only a trace of starting material. The reaction mixture is then concentrated in vacuo to a pale semi-solid. This is partitioned between 100 ml of methylene chloride and ca 30 ml of 3 N sodium hydroxide. The aqueous phase is back extracted with 100 ml of methylene chloride. The organic phases are combined, washed with 50 ml of brine, dried over potassium carbonate and concentrated in vacuo to pale yellow oil. This oil is crystallized from hexane with a little methylene chloride to give end product of m.p. 115°–119° C.

EXAMPLE 5

2-Methyl-1[4-chlorophenyl)-2[(2-fluorobenzyl)-methyl]]-1H-imidazole-5-carboxaldehyde To a stirred suspension of 98.7 g (0.357 mole) of 4-chloro-2[(2-fluorophenyl)methyl]-N-(1-aminoethylidene)benzenamine in 500 ml of 2-(propanol) is added 55 g (0.364 mole) of bromomalonaldehyde, 250 ml of 2-propanol, 25 ml of glacial acetic acid, and 59 ml of triethylamine. The mixture is stirred and heated under reflux for 1 hr to give an orange solution. It is cooled to r.t. overnight and concentrated in vacuo to an orange residue. This is poured into 2 l. of ice water and 100 ml of ether, containing seeds of product with stirring. This mixture is stirred ca. 2 hr until the product has solidified and most of the ether evaporated. The product is collected and washed with water and with hexane to give crude product.

This was used as is for the next step. An analytical sample prepared by recrystallization from hexane had m.p. 88°–90° C.

EXAMPLE 6

2-Methyl-1-[4-chlorophenyl-2-[(2-fluorophenyl)-methyl]]-1H-imidazole-5-methanol To a stirred suspension of 140 g (containing 0.357 mole) of crude 2-methyl-1-[4-chlorophenyl-2-[(2-fluorophenyl)-methyl]]-1H-imidazole-5-carboxaldehyde in 1 l. of methanol cooled to 10° C. was added 27.6 g (0.73 mole) of sodium borohydride in portions during 10 min. the temperature rose to 15° C. The reaction mixture was stirred at room temperature for 1 hr was then neutralized to pH with glacial acetic acid. It was concentrated in vacuo to a thick slurry and then diluted with water with cooling and stirring. After stirring overnight the precipitate was collected, washed with water and dried to give end product of m.p. 152°–155° C.

EXAMPLE 7

5-(Chloromethyl)-2-methyl-1-[4-chloro-2-(2-fluorobenzyl)phenyl]-1H-imidazole To a stirred solution of 100 g (0.303 mole) of 2-methyl-1-[4-chlorophenyl-2-[(2-fluorophenyl)-methyl]-1H-imidazole-5-methanol in 1 l. of chloroform cooled to 10° C. was added 43.2 g (0.363 mole) of thionyl chloride over a ¼ hr period. The temperature was maintained at 10°–20° C. by means of an ice-water bath during this addition. The bath was removed and stirring was continued for 2 hr. The solution was concentrated in vacuo to give a solid residue. The solid residue was taken up in 400 ml of methylene chloride which was filtered by gravity. To this solution was added 400 ml of ether. The resulting precipitate was collected and dried in vacuo overnight to give end product of m.p. 169°–172° C. dec.

EXAMPLE 8

2-[[2-Methyl-1-[4-chloro-2-(2-fluorobenzyl)phenyl]-1H-imidazol-5-yl]methyl]-1H-isoindole-1,3(2H)dione To a suspension of 89.4 g (0.232 mole) of 5-(chloromethyl)-2-methyl-1-[4-chloro-2-(2-fluorobenzyl)phenyl]-1H-imidazole in 900 ml of tetrahydrofuran cooled to 10° C. was added 26.2 g (0.232 mole) of potassium t-butoxide. The temperature was maintained at 20° C. by means of an ice water bath during this addition. The bath was removed. To this mixture was added 51.5 g (0.278 mole) of potassium phthalimide. The reaction mixture was stirred under reflux for 2 hr. The mixture was cooled to room temperature and poured onto 1.2 l. of ice-water and extracted with 3×600 ml of methylene chloride. The organic phases were combined and dried over sodium sulfate. The solution was filtered free of drying agent and the filtrate concentrated to dryness giving an oil. The oil was crystallized from 180 ml of ether. The resulting crystals were collected and dried to give end product of m.p. 152°–156° C.

EXAMPLE 9

2-[[2-Methyl-1-[4-chloro-2-(2-fluorobenzoyl)phenyl]-1H-imidazol-5-yl]methyl]-1H-isoindole-1,3(2H)-dione To a solution of 53.1 g (0.116 mole) of 2-[[2-methyl-1-[4-chloro-2-(2-fluorobenzyl)phenyl]-1H-imidazol-5-yl]methyl]-1H-isoindole-1,3(2H)-dione in 600 ml of glacial acetic acid was added with stirring a chromic acid solution made from 69.3 g (0.693 mole) of chromium trioxide, 200 ml of water and 61.2 ml of concentrated sulfuric acid. The reaction mixture was then stirred for 4 hr with heating on a steam bath. It was cooled below 25° C. and the excess chromic acid destroyed by the slow addition of 300 ml of 2-propanol while keeping the temperature below 25° C. It was neutralized by the addition of 3 l. of 6 N sodium hydroxide with cooling to maintain the temperature below 20° C. The reaction mixture was then extracted with 6×600 ml of methylene chloride. The organic extracts were combined, washed with 2×750 ml of water and 750 ml of brine and dried over magnesium sulfate. The residue left on concentration of this solution in vacuo was crystallized from ether to give end product of m.p. 192°–196° C.

An analytical sample from ethyl acetate had m.p. 196°–199° C.

EXAMPLE 10

8-Chloro-6-(2-fluorophenyl)-1-methyl-4H-imidazo[1,5-a][1,4]benzodiazepine

To a stirred suspension of 2-[[2-methyl-1-[4-chloro-2-(2-fluorobenzoyl)phenyl]-1H-imidazol-5-yl]mehtyl]-1H-isoindole-1,3(2H)-dione in 175 ml of ethanol (2B) was added 55.2 ml of 40% aqueous methyl amine solution. After 1 hr a solution resulted. The reaction mixture was kept overnight at room temperature. It was concentrated in vacuo. The residue was slurried with 350 ml of ethyl acetate. The solid was filtered off and the filtrate concentrated in vacuo. The residue was again slurried with ethyl acetate and the solid filtered off. The filtrate was concentrated in vacuo to an oil which was dissolved in 75 ml of hot ethanol. To this was added 9.8 g (84.5 mmole) of maleic acid dissolved in 10 ml of hot ethanol. The resulting solution was diluted with 175 ml of ether and cooled in an ice bath to yield the end product as crude, m.p. 110°–115° C. Recrystallization from ethanol/ether gave purified product, m.p. 114°–117° C.

What is claimed:

1. A compound of the formula wherein X and Y are selected from the group consisting of hydrogen, halogen and trifluoromethyl.

2. A compound of the formula where X and Y are selected from the group consisting of hydrogen, halogen and trifluoromethyl.

* * * * *